United States Patent [19]
Janchitraponvej et al.

[11] Patent Number: 5,556,615
[45] Date of Patent: *Sep. 17, 1996

[54] CLEAR CONDITIONING COMPOSITION

[75] Inventors: Ben Janchitraponvej, Niles; William J. Brown, Flossmoor; Patricia Lee, Chicago, all of Ill.

[73] Assignee: Helene Curtis, Inc., Chicago, Ill.

[*] Notice: The term of this patent shall not extend beyond the expiration date of Pat. No. 5,328,685.

[21] Appl. No.: 240,010

[22] Filed: May 9, 1994

Related U.S. Application Data

[62] Division of Ser. No. 40,116, Mar. 30, 1993, Pat. No. 5,328,685.

[51] Int. Cl.$^6$ .................................................. A61K 7/075
[52] U.S. Cl. .............. 424/70.11; 510/122; 510/126; 510/466; 510/501; 510/488; 510/500; 510/477
[58] Field of Search ................. 424/70.11, 70.12, 424/70.27; 252/174.15, 544, 547, 174.23, DIG. 2, DIG. 13

[56] References Cited

U.S. PATENT DOCUMENTS

| | | | |
|---|---|---|---|
| 3,993,744 | 11/1976 | Cella et al. | 424/70 |
| 4,275,055 | 6/1981 | Nachtigal et al. | 474/70 |
| 4,597,964 | 7/1986 | Ziemelis et al. | 424/70 |
| 4,601,902 | 7/1986 | Fridd et al. | 424/70 |
| 4,725,433 | 2/1988 | Matravers | 474/70 |
| 4,777,037 | 10/1988 | Wagman et al. | 474/70 |
| 4,933,176 | 6/1990 | Van Reeth | 424/70 |
| 4,940,576 | 7/1990 | Walsh | 424/70.11 |
| 4,954,335 | 9/1990 | Janchitraponvej et al. | 424/70.28 |
| 4,976,956 | 12/1990 | Noe | 424/70 |
| 5,077,041 | 12/1991 | Yamashina et al. | 424/70 |
| 5,098,979 | 3/1992 | O'Lenick, Jr. | 528/15 |
| 5,100,657 | 3/1992 | Ansher-Jackson et al. | 424/70 |
| 5,306,434 | 4/1994 | Schueller et al. | 252/8.8 |

OTHER PUBLICATIONS

STN, CAS, Registry File, as of Jan. 24, 1996, RN's 125052-34-8, 125052-35-9, 134737-05-6, 157971-46-5. All Structural Formulae not available.

*Primary Examiner*—Melvyn I. Marquis
*Assistant Examiner*—Robert H. Harrison
*Attorney, Agent, or Firm*—Marshall, O'Toole, Gerstein, Murray & Borun

[57] ABSTRACT

A method of imparting improved conditioning properties to hair comprising treating the hair with a clear conditioning composition comprising an amidoamine salt, said amidoamine salt comprising an amidoamine compound having the general structural formula:

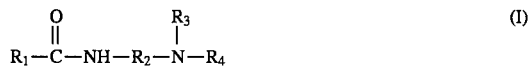

(I)

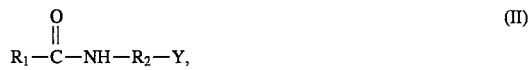

(II)

neutralized with a suitable acid, wherein $R_1$ is a fatty acid chain having about 11 to about 21 carbon atoms, $R_2$ is an alkylene group having two to about four carbon atoms, $R_3$ is hydrogen, methyl, ethyl or a hydroxyalkylene group having one to about three carbon atoms, $R_4$ is methyl, ethyl or a hydroxyalkylene group having one to about three carbon atoms, and Y is a heterocyclic nitrogen-containing moiety, like morpholine or pyridine; and a silicone compound having at least one quaternary ammonium moiety.

19 Claims, No Drawings

CLEAR CONDITIONING COMPOSITION

CROSS-REFERENCE TO RELATED APPLICATIONS

This application is a divisional of U.S. patent application Ser. No. 08/040,116, filed Mar. 30, 1993, now U.S. Pat. No. 5,328,685.

FIELD OF THE INVENTION

The present invention relates to a clear conditioning composition and to a method of treating hair that imparts improved conditioning properties to hair. More particularly, the present invention is directed to a clear conditioning composition comprising about 0.4% to about 15% by weight of an amidoamine salt, said amidoamine salt comprising an amidoamine compound neutralized with a suitable acid and having the general structural formula (I) or (II):

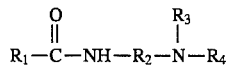

(I)

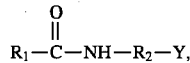

(II)

wherein $R_1$ is a fatty acid chain having about 11 to about 21 carbon atoms, $R_2$ is an alkylene group having two to about four carbon atoms, $R_3$ is hydrogen, methyl, ethyl or a hydroxyalkylene group having one to about three carbon atoms, $R_4$ is methyl, ethyl or a hydroxyalkylene group having one to about three carbon atoms, and Y is a heterocyclic nitrogen-containing moiety, like morpholine or pyridine; and about 0.1% to about 5% by weight of a silicone compound having at least one quaternary ammonium moiety, wherein the amidoamine compound is present in a sufficient amount to solubilize the silicone compound in an aqueous carrier and to provide a clear, translucent to transparent composition. The resulting clear, conditioning composition can be applied to the hair from an aqueous solution or spray, a conditioner formulation, a hair color or other similar hair treatment product, over a pH range of about 4 to about 7, to improve both the wet stage and the dry stage properties of the hair.

BACKGROUND OF THE INVENTION

Most individuals buy and use a hair shampoo for its cleansing properties. In addition to having clean hair, a consumer also desires sufficiently-conditioned hair that holds a preset configuration. However, hair shampoos generally are formulated with highly effective anionic surfactants that primarily clean as opposed to conditioning in the hair. Anionic surfactants not only remove the dirt and soil from the hair, but also remove sebum naturally present on the surface of the hair fibers. Therefore, the desirable cleansing properties of anionic surfactants also leave the hair in a cosmetically-unsatisfactory condition. Shampoos also do not detangle wet hair and do not impart residual conditioning benefits to dry hair, such as manageability or styleability of hair sets.

In general, shampoo compositions containing anionic surfactants, or nonionic surfactants or amphoteric surfactants, leave hair with an undesirable harsh, dull and dry touch, or feel, usually called "creak", after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing property of dry hair remains poor, and the hair has undesirable electrostatic properties in a low humidity atmosphere that causes the hair to "fly away", thereby further reducing the brushing properties of the hair.

The unsatisfactory combing or brushing property of hair immediately after shampooing, or during trimming treatments after shampooing, also causes hair damage, such as split ends or hair breakage. In addition, the natural luster and resiliency of the hair is reduced. The overall unsatisfactory condition of shampooed hair often necessitates a subsequent post-shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. The wet combing problem has been solved by treating shampooed hair with a conditioner composition that coats the hair shaft and causes the individual hair shafts in a tress to resist tangling and matting because of the conditioner residue retained on the shaft.

However, the need for improved compositions that condition the hair, i.e., render the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair often are used to complete the hair cleansing and hair conditioning cycle.

The ability of cationic compounds to adsorb to or interact with the keratinous material of the hair makes these compounds desirable for improving wet hair detangling and dry hair manageability. However, cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought.

For example, the majority of present-day, commercial hair-conditioner compositions are emulsion-type products. Emulsion products have been preferred because a water-insoluble hair conditioning compound, which resists rinsing from the hair during the rinsing step, can be formulated into a conditioner composition. However, such water-insoluble conditioning compounds often leave an excessive residue of conditioning compound on the hair.

Consequently, the present invention is directed to a new clear conditioning composition that is esthetically acceptable to consumers, improves the wet combing and dry combing properties of hair, and also leaves the dry hair with satisfactory cosmetic and physical properties, including, in particular, dry combing and feel, less hair coating, manageability, body, condition of the ends and set.

Effective clear conditioning compositions have been difficult to formulate because conditioning compounds used in clear conditioning compositions often have a relatively high water solubility and are too easily rinsed from the hair. Therefore, investigators have continually sought a clear conditioning composition incorporating a conditioning compound that provides a clear composition yet is not easily rinsed from the hair.

Hair conditioning compositions, such as emulsion-type creme rinses, are well known in the art for improving the combing properties of wet hair and dry hair. These conditioning compositions typically are aqueous emulsions including a cationic compound, like a quaternary ammonium compound, as the principal conditioning agent. Prior patents describe the quaternary ammonium compound either as a polymeric material having a plurality of quaternary nitrogen atoms per molecule or as a molecule having at least one long carbon chain and an average of one quaternary nitrogen atom per molecule. The prior patents also describe hair conditioning compositions as including silicon-containing compounds, substituted amides and amides, nonionic surfactants, long carbon chain alcohols and esters, and other ingredients to facilitate composition formulation and enhance consumer appeal.

For example, Cella et al. U.S. Pat. No. 3,993,744 discloses that cationic compounds, such as quaternary ammonium compounds, and silicones can be combined with perfluorinated compounds to provide hair treatment compositions. The silicones specifically disclosed by Cella et al. are nonionic surfactant-like polyoxyethylene polymethylsiloxanes that apparently are water-soluble or dispersible.

Matravers U.S. Pat. No. 4,725,433 discloses a clear conditioning composition comprising an aqueous blend of a polymeric quaternary ammonium salt, ethoxylated lauryl alcohol, ethoxylated cholesterol and hydroxyethylcellulose.

Janchipraponvej U.S. Pat. No. 4,954,335 discloses a clear conditioning composition comprising a quaternary ammonium compound, an amidoamine, a volatile conditioning agent and a solubilizing nonionic surfactant.

Nachtigal et al. U.S. Pat. No. 4,275,055 discloses a pearlescent hair conditioner composition including a quaternized tertiary amidoamine, a quaternary ammonium compound and, optionally, a tertiary amidoamine, i.e., stearamidoethyldiethylamine. The composition of Nachtigal et al. is directed to achieving a stable pearlescent effect and neither includes a silicone compound having at least one quaternary ammonium moiety nor is the composition a clear conditioning composition.

Wagman et al. U.S. Pat. No. 4,777,037 discloses a hair conditioner composition comprising a polydimethyl cyclosiloxane, a quaternary-nitrogen containing conditioning agent having two long alkyl chains of twelve to eighteen carbons and two short alkyl chains of one or two carbon atoms, a long chain fatty alcohol and a tertiary amidoamine of the general structural formula (III):

wherein $R_8$ is a fatty chain having from about 11 to about 17 carbon atoms, $R_9$ is an alkylene group having 2 or 3 carbon atoms and $R_{10}$ is methyl or ethyl. The compositions of Wagman et al. are emulsions as opposed to the clear conditioning compositions of the present invention.

Ziemelis et al. U.S. Pat. No. 4,597,964 discloses a cationic polyorganosiloxane that is substantive to protein substrates. The disclosed cationic organosiloxanes are emulsifiable and are used to treat hair.

As will be demonstrated more fully hereinafter, and in contrast to prior emulsion-type hair-conditioning compositions, a clear conditioning composition of the present invention, comprising: (1) an amidoamine salt, said amidoamine salt comprising: (a) an amidoamine compound of general structural formula (I) or (II), (b) neutralized with a suitable acid, and (2) a silicone compound having at least one quaternary ammonium moiety, unexpectedly imparts improved conditioning properties upon application to human hair. Therefore, the condition of treated hair is improved by a method of contacting the hair with a clear aqueous composition comprising an amidoamine compound of general structural formula (I) or (II) neutralized with a suitable acid, and a silicone compound having at least one quaternary ammonium moiety. A composition of the present invention can be applied to the hair from an aqueous carrier at ambient temperature and is allowed to contact the hair for a relatively short time to provide the benefits and advantages of a hair conditioner. Consequently, the method and composition of the present invention condition the hair to provide more manageable and esthetically-pleasing hair.

SUMMARY OF THE INVENTION

In brief, the present invention relates to a composition and method of treating hair. More particularly, the present invention relates to a method of treating the hair, whereby the hair is conditioned by contacting the hair with a clear, homogeneous conditioning composition comprising: (1) an amidoamine amine salt comprising (a) an amidoamine compound neutralized with (b) a suitable acid, wherein the amidoamine compound has the general structural formula (I) or (II), or a mixture thereof:

wherein $R_1$ is a fatty acid chain having about 11 to about 21 carbon atoms, $R_2$ is an alkylene group having two to about four carbon atoms, $R_3$ is hydrogen, methyl, ethyl or a hydroxyalkylene group having one to about three carbon atoms, $R_4$ is methyl, ethyl or a hydroxyalkylene group having one to about three carbon atoms, and Y is a heterocyclic nitrogen-containing moiety; and (2) a silicone compound having at least one quaternary ammonium moiety, such as for example a cationic organosiloxane having the general structural formula (IV):

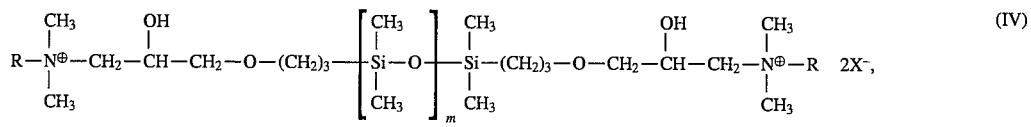

wherein R is an alkyl group having one to about twenty-two carbon atoms, m is a numeral from about five to about fifty, and X is a water-soluble anion in (3) an aqueous carrier, wherein the amidoamine compound is present in a sufficient amount to solubilize the silicone compound. The easy-to-apply clear composition is esthetically pleasing for consumer acceptance, imparts excellent wet stage and dry stage conditioning properties to the hair, and is easily rinsed from the hair. Surprisingly and unexpectedly, hair treated with a clear conditioner composition of the present invention also demonstrates improved physical and cosmetic properties, such as wet and dry feel, less coating, thickness, overall hair condition, manageability and body.

Therefore, one aspect of the present invention to provide a clear conditioning composition that conditions the hair and imparts improved physical and cosmetic properties to the hair. The clear conditioning composition is translucent to transparent to improve consumer acceptance, is easily applied to and rinsed from the hair, and deposits a sufficient residual amount of the conditioner on the hair to condition the hair.

Another aspect of the present invention to provide a clear conditioning composition comprising an amidoamine salt, said amidoamine salt comprising an amidoamine compound having general structural formula (I) or (II) neutralized with a suitable acid, and a silicone compound having at least one quaternary ammonium moiety, such as, for example, a cationic organosiloxane having the general structural formula (IV).

Another aspect of the present invention is to provide an aqueous clear conditioning composition that is capable of conditioning the hair and imparting improved physical and cosmetic properties to the hair at a pH of about 4 to about 7.

Another aspect of the present invention is to provide a method of treating hair with a clear conditioning composition to improve the condition of the hair.

Another aspect of the present invention is to provide a method of treating hair by contacting the hair with a clear conditioning composition having a pH of about 4 to about 7 and comprising an amidoamine compound of general structural formula (I) or (II) neutralized with a suitable acid, and a silicone compound having at least one quaternary ammonium moiety; then drying the hair, to condition the hair and to impart improved physical and cosmetic properties to the hair.

Another aspect of the present invention is to provide a method of treating hair to yield well-conditioned hair by contacting the hair with a clear conditioning composition comprising: (a) about 0.4% to about 15% by weight of an amidoamine salt, said amidoamine salt comprising an amidoamine compound having the general structural formula (I) or (II) neutralized with a suitable acid, and (b) about 0.1% about 5% by weight of a silicone compound having at least one quaternary ammonium moiety, such as for example a cationic organosiloxane having the general structural formula (IV), in (c) an aqueous carrier, wherein a sufficient amount of the amidoamine compound is present to solubilize the silicone compound and provide a clear conditioning composition.

Another aspect of the present invention is to provide a method of treating hair to yield unexpectedly well conditioned hair by contacting the hair with a composition comprising about 0.4% to about 15% by weight lauramidopropyldimethylamine, an amidoamine compound of general structural formula (I) having the structural formula (V):

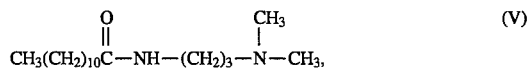

neutralized with a suitable acid, like lactic acid; and (b) about 0.1% to about 5% by weight of a cationic organosiloxane of general structural formula (IV) having the structural formula (VI):

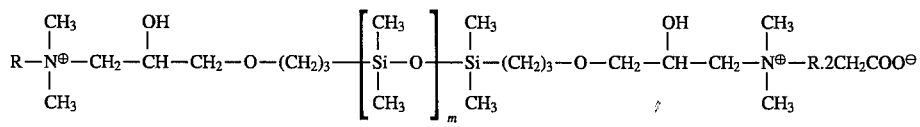

wherein R is an alkyl group having 1 to about 22 carbon atoms and m is an integer from about 5 to about 30, or a silicone polymer having at least one pendant quaternary ammonium moiety, or a mixture thereof.

Another aspect of the present invention is to provide a new and improved clear conditioning composition capable of conditioning the hair and imparting improved physical, cosmetic and esthetic properties both to normal hair and to tinted, frosted, bleached or other substantially-damaged hair.

Still another aspect of the present invention is to provide a method of treating the hair to yield well-conditioned hair having esthetically-pleasing physical properties by contacting the hair with a clear, aqueous spray or solution to treat the hair, without heat, in either a rinse-off or leave-on method.

DETAILED DESCRIPTION OF THE PREFERRED EMBODIMENT

A clear conditioning composition of the present invention comprises: (a) an amidoamine salt comprising an amidoamine compound having the general structural formula (I) or (II):

neutralized with a suitable acid, wherein $R_1$ is a fatty acid chain having about 11 to about 21 carbon atoms, $R_2$ is an alkylene group having about two to about four carbon atoms, $R_3$ is hydrogen, methyl, ethyl or a hydroxyalkylene group having one to about three carbon atoms, $R_4$ is methyl, ethyl or a hydroxyalkylene group having one to about three carbon atoms, and Y is a heterocyclic nitrogen-containing moiety, like morpholine or pyridine; and (b) a silicone compound having at least one quaternary ammonium moiety, such as for example a cationic organosiloxane having the general structural formula (IV):

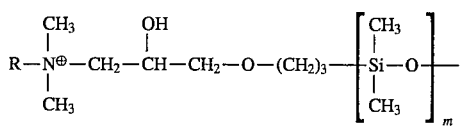 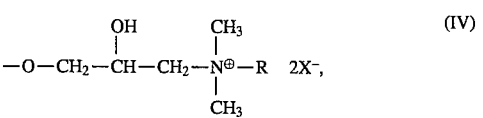 (IV)

wherein R is an alkyl group having one to about 22 carbon atoms, m is a numeral from about five to about fifty, and X is a water-soluble anion, in (c) an aqueous carrier, wherein the amidoamine compound is present in a sufficient amount to solubilize the silicone compound and provide a clear composition. The easy-to-apply, clear conditioning composition imparts excellent wet comb and dry comb properties to the hair, and the hair demonstrates improved physical and cosmetic properties, such as gloss, thickness, softness, manageability, body and less coating.

A composition of the present invention includes about 0.4% to about 15%, and preferably about 0.7% to about 8%, by weight of an amidoamine salt. To achieve the full advantage of the present invention, the clear conditioning shampoo includes about 0.8% to about 5% by weight of the amidoamine salt.

An amidoamine salt useful in the present invention comprises an amidoamine compound having the general structural formula (I) or (II):

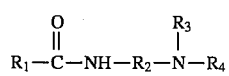 (I)

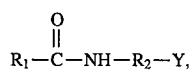 (II)

neutralized with a suitable acid, wherein $R_1$ is a fatty acid chain having about 11 to about 21 carbon atoms, $R_2$ is an alkylene group having two to about four carbon atoms, $R_3$ is hydrogen, methyl, ethyl or a hydroxyalkylene group having one to about three carbon atoms, $R_4$ is methyl, ethyl or a hydroxyalkylene group having one to about three carbon atoms, and Y is a heterocyclic nitrogen-containing moiety, like morpholine. The amidoamine salt is present in the clear conditioning composition in a sufficient amount to solubilize the silicone compound in the aqueous carrier. Therefore, the primary function of the amidoamine salt is to act as a solubilizer. However, the amidoamine salt also helps impart improved physical and cosmetic properties to the hair.

Nonlimiting examples of amidoamine compounds having general structural formula (I) that are useful in the composition and method of the present invention are compounds designated in the *CTFA Cosmetic Ingredient Dictionary, Fourth Edition* (1991), hereinafter the *CTFA Dictionary*, as lauramidopropyldimethylamine and stearamidopropyldimethylamine, available commercially under the tradenames LEXAMINE L-13 and LEXAMINE S-13, respectively, from Inolex Chemical Div., Philadelphia, Pa., and having the structural formulae (V) and (VII), respectively:

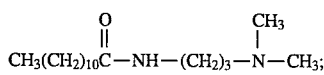 (V)

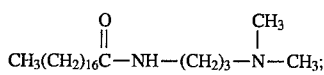 (VII)

Other exemplary amidoamine compounds include, but are not limited to, compounds designated in the *CTFA Dictionary* as stearamidoethyldiethanolamine, isostearamidopropylmorpholine, stearamidopropylmorpholine, and stearamidoethylethanolamine, having structural formulas (VIII), (IX), (X), and (XI), respectively. In addition, other suitable amidoamine

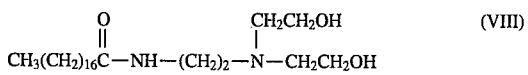 (VIII)

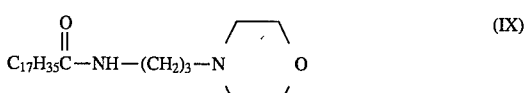 (IX)

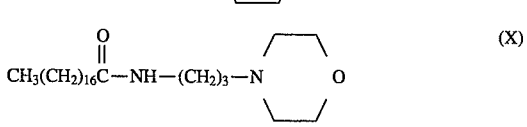 (X)

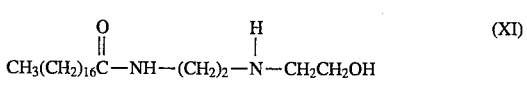 (XI)

compounds have either one or two hydroxymethyl, hydroxypropyl, methyl or ethyl moieties, or mixtures thereof, present on an amino nitrogen in place of the hydroxyethyl moieties. Examples of such amidoamine compounds include, but are not limited to, diethylaminoethylstearamide, isostearamidopropyldimethylamine, cocamidopropyldimethylamine, ricinoleamidopropyldimethylamine, oleamidopropyldimethylamine, behenamidopropyldimethylamine, wheat germamidopropyldimethylamine, palmitamidopropyldimethylamine, stearamidoethyldiethylamine, soyamidopropyldimethylamine, and dimethylaminopropyl myristamide.

The fatty acid chain $R_1$ of amidoamine compounds of general structural formulas (I) and (II) does not have to be solely, or primarily, of one chain length, i.e., the long chain need not be derived only from lauryl ($C_{12}$), myristyl ($C_{14}$), cetyl ($C_{16}$), or stearyl ($C_{18}$). Rather, amidoamine compounds of general structural formulas (I) and (II) wherein the long alkyl chain is a mixture of lengths can be used. Such amidoamine compounds are prepared conveniently from naturally-occurring materials, such as tallow, coconut oil, soya oil and the like, or from synthetically produced mixtures.

In accordance with an important feature of the present invention, after adjustment of the pH with a suitable acid, the above-described amidoamine compounds of general structural formulae (I) or (II) exhibit the properties of a cationic surfactant. In the free amine state, as depicted in structural formulae (I), (II), (V) and (VII) through (XI), the amidoamine compounds generally are insoluble in water. However, after pH adjustment, the amidoamine compounds exhibit increased water solubility. In the neutralized state, an amidoamine salt also behaves like a cationic surfactant, and therefore is substantive to the hair and imparts conditioning properties to the hair. In the present invention, an amidoamine salt primarily acts to solubilize the silicone compound to provide a clear conditioning composition.

The acid used to adjust the pH of the amidoamine composition and the composition is essentially any organic acid or mineral acid. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or combinations thereof. To achieve the full advantage of the present invention, the composition pH is adjusted with an organic acid, like lactic acid or tartaric acid. In general, a sufficient amount of acid is added to adjust the final pH of the clear conditioning composition to about 4 to about 7, and preferably to about 4.5 to about 6.5. Typically, the weight amount of acid added to the composition is less than one half of the weight amount of amidoamine compound added to the composition.

In addition to the amidoamine salt, the clear conditioning composition also includes about 0.1% to about 5%, and preferably about 0.2% to about 4%, by weight of a silicone compound having at least one quaternary ammonium moiety. Preferably, the silicone compound has at least two quaternary ammonium moieties. To achieve the full advantage of the present invention, the clear conditioning composition includes about 0.2% to about 3% by weight of a silicone compound having at least one quaternary ammonium moiety.

An example of a silicone compound having at least one quaternary ammonium moiety is depicted by general structural formula (IV):

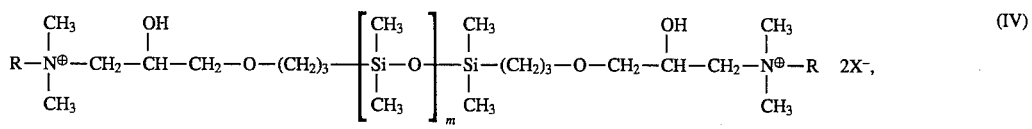

wherein R is an alkyl group having one to about 22 carbon atoms, m is a numeral from five to about fifty, and X is a water-soluble anion, either organic or inorganic, such as chloride or acetate. A silicone compound having at least one quaternary ammonium moiety, such as the compound depicted in the general structural formula (IV), exhibits properties of a silicone and a quaternary ammonium compound, and imparts conditioning properties to the hair.

A specific example of a silicone compound having general structural formula (IV) that is useful in the composition and method of the present invention is designated in the *CTFA Dictionary* as Quaternium-80, available commercially under the tradename ABIL-QUAT 3270 and ABIL-QUAT 3272 from Goldschmidt Chemical Corporation, Hopewell, Va., and having the structural formula (VI):

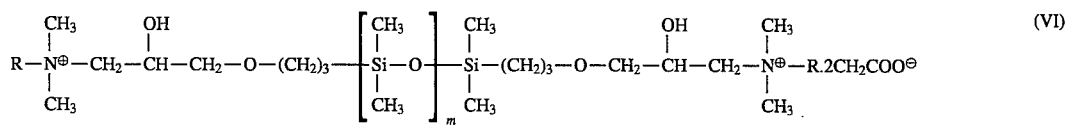

wherein R is an alkyl group having one to about 22 carbon atoms, and m is about 10 or about 30 for ABIL-QUAT 3270 and ABIL-QUAT 3272, respectively.

Other silicone compounds having at least one quaternary ammonium moiety that can be used in the present clear conditioning composition are disclosed in O'Lenick, Jr. U.S. Pat. No. 5,098,979, incorporated herein by reference. The disclosed silicone compounds are polymers having a silicone backbone with at least one quaternary ammonium moiety as a pendant group. The quaternary ammonium moiety can be an alkylamido group or an imidazoline group. In particular, the silicone compounds disclosed in O'Lenick, Jr. U.S. Pat. No. 5,098,979 have the general structural formula (XII):

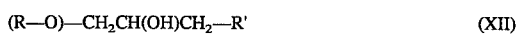

(XII)

wherein R is

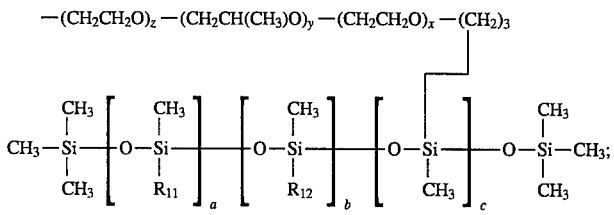

a and b independently are integers from 0 to 200;

c is an integer from 1 to 200;

x, y and z independently are integers each ranging from 0 to 20 with the proviso that the sum of x, y and z is at least 1;

$R_{11}$ is selected from $-(CH_2)_w CH_3$ and phenyl, wherein w is an integer from 0 to 10;

$R_{12}$ is selected from $-(CH_2)_3-(OCH_2CH_2)_r-(OCH_2CH(CH_3))_s-(OCH_2CH_2)_t-OH$, wherein r, s and t are integers independently selected from 0 to 20; R' is selected from

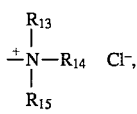

wherein $R_{13}$, $R_{14}$ and $R_{15}$ independently each are alkyl groups having from 1 to 20 carbon atoms;

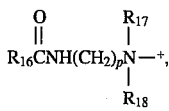

wherein $R_{16}$ is an alkyl group having from 6 to 20 carbon atoms, $R_{17}$ and $R_{18}$ are independently selected from the group consisting of methyl and ethyl, and p is an integer from 1 to 5; and

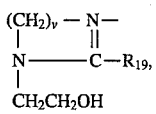

wherein $R_{19}$ is an alkyl group having from 6 to 20 carbon atoms and v is an integer from 1 to 5.

Silicone compounds depicted by general structural formula (XII) are available commercially from Siltech Inc., Norcross, Ga. under the tradename SILQUAT. Particular silicone compounds of general structural formula (XII) are SILQUAT Q-50, SILQUAT Q-100, SILQUAT Q-200 and SILQUAT Q-300. The SILQUAT silicone compounds differ primarily in the moles of ethoxylation and/or propoxylation present in the compound, with SILQUAT Q-50 having the fewest moles of ethoxylation and/or propoxylation in comparison to the other SILQUAT silicone compounds. Accordingly, SILQUAT Q-50 is the most hydrophobic of the SILQUAT silicone compounds.

In accordance with an important feature of the present invention, a hydrophobic silicone compound of general structural formula (XII) is preferred in the clear conditioning composition of the present invention. A preferred hydrophobic silicone compound of general structural formula (XII) has a sum of the terms x, y, z, r, s and t of 1 to about 80. To achieve the full advantage of the present invention, a silicone compound of general structural formula (XII) has a sum of the terms z, y, z, v, s and t of 1 to about 50.

The hydrophobic silicone compounds are preferred because such compounds are effectively deposited on the hair to condition the hair and resist rinsing from the hair during the rinse step. Surprisingly, the hydrophobic silicone compounds can be incorporated into the present composition to provide a clear conditioning composition.

The relative amounts of the amidoamine compound and of the silicone compound having at least one quaternary ammonium moiety in the composition is sufficient to solubilize the silicone compound and provide a clear conditioning composition. Therefore, to provide a clear conditioning composition, the weight ratio of amidoamine compound to silicone compound is at least about 2.8 to 1, and preferably about 3 to 1 to about 4 to 1. At such weight ratios, the silicone compound is sufficiently solubilized by the neutralized amidoamine compound, yet is effectively deposited on the hair shaft to condition the hair. A weight ratio of an amidoamine compound to silicone compound greater than about 4 to 1 is not especially detrimental to the composition, but also is not necessary to achieve a clear condition composition. In addition an excessive amount of amidoamine compound can solubilize the silicone compound to such a degree that the silicone compound is easily rinsed from the hair. Accordingly, product performance could decrease.

In accordance with another important feature of the present invention, a clear conditioning composition is provided when the weight ratio of amidoamine compound to silicone compound is at least 2.8 to 1, even in the absence of a coupling agent like hexylene glycol. However, if desired, a coupling agent optionally can be included in the clear conditioning composition without adversely affecting the composition or its ability to condition the hair.

In addition to the above-described essential ingredients, other common cosmetic components and additives can be incorporated in the clear conditioning composition with the essential ingredients, as long as the basic properties of the composition, such as clarity of the composition and an ability to condition the hair, are not adversely affected. Such optional ingredients include, but are not limited to, humectants, inorganic salts, fragrances, dyes, hair colorants, hydrotropes, foam stabilizers, preservatives, water softening agents, acids, bases, buffers and the like. Optional components usually are present in weight percentages of less than about 2% each, and from about 5% to about 10% by weight of the composition in total.

Other optional ingredients can be included in the clear conditioning composition to enhance the ability of the composition to condition the hair. For example, other quaternary ammonium compounds can be included in the clear conditioning composition. A quaternary ammonium compound useful in the composition of the present invention preferably is a water-soluble quaternary ammonium compound having one or two long chain alkyl groups containing from about 8 to about 18 carbon atoms. The long chain alkyl groups also can include, in addition to, or as a substitute for, carbon and hydrogen atoms, ether linkages or similar water-solubilizing linkages. The remaining two to three substitutes of the quaternary nitrogen of the quaternary ammonium compound can be hydrogen; or benzyl; or short chain alkyl or hydroxyalkyl groups such as methyl, ethyl, hydroxymethyl or hydroxyethyl groups; or mixtures thereof, either of the same or of different identity. However, an oil-soluble, water dispersible quaternary ammonium compound, either alone or in combination with a water-soluble quaternary ammonium compound, also can be used in the composition of the present invention.

An exemplary quaternary ammonium compound is dicetyldimonium chloride, available commercially from Sherex Chemical Co., Dublin, Ohio, under the tradename ADOGEN 432-ET. Other useful quaternary ammonium compounds include lauryltrimethylammonium chloride, stearyltri(2-hydroxyethyl)ammonium chloride, lauryldimethylbenzylammonium chloride, oleyldimethylbenzylammonium chloride, dilauryldimethylammonium chloride, cetyldimethylbenzylammonium chloride, dicetyldimethylammonium chloride, laurylpyridinium chloride, and cetylpyridinium chloride. A quaternized protein-based quaternary ammonium compound, such as a quaternized wheat-based protein sold under the tradename MACKPRO WLW, available from The McIntyre Group, University Park, Ill., also can be used in the present clear conditioning composition.

The clear conditioning composition also can include a water-insoluble conditioning agent, like a nonquaternized silicone or a hydrocarbon conditioning agent. Preferably, the water-insoluble conditioning agent is a volatile conditioning agent. An example of a silicone compound useful in the composition and method of the present invention is a volatile polydimethylsiloxane compound, for example a compound designated in the *CTFA Dictionary* as hexamethyldisiloxane, available commercially under the tradename DOW CORNING 200 FLUID, from Dow Corning Corp., Midland, Mich. In addition, a cyclic volatile polydimethylsiloxane, designated in the *CTFA Dictionary* as a cyclomethicone, is useful in the clear conditioning composition of the present invention. The cyclomethicones are low molecular weight, water-insoluble cyclic compounds having an average of about 3 to about 6 —[O—Si(CH$_3$)$_2$]— repeating group units per molecule. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y. and SILICONE 334 FLUID and SILICONE 345 FLUID from Dow Corning Corporation, Midland, Mich.

The optional water-insoluble conditioning agent included in the composition of the present invention also can be a volatile hydrocarbon, such as a hydrocarbon including from about 10 carbon atoms to about 26 carbon atoms. Such hydrocarbons have sufficient volatility to slowly volatilize from the hair and therefore a residual buildup of hydrocarbon is not present on dry hair. The volatile hydrocarbon provides essentially the same benefits as the volatile silicone, such as lubrication and wet hair conditioning.

The preferred volatile hydrocarbon compound is an aliphatic hydrocarbon including from about 12 to about 24 carbon atoms, and has a boiling point in the range of from about 100° C. to about 300° C. Exemplary volatile hydrocarbons are depicted in general structural formula (XIII), wherein d ranges from 2 to 5.

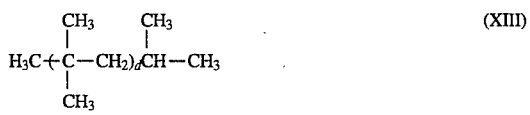

(XIII)

Nonlimiting examples of volatile hydrocarbons useful in the clear conditioning composition of the present invention are commercially-available compounds PERMETHYL 99A and PERMETHYL 101A, corresponding to compounds of general structure (XIII) wherein d is 2 and 3, respectively, from Permethyl Corporation, Frazer, Pa. A volatile hydrocarbon compound is useful in the clear hair-conditioning composition of the present invention either alone, in combination with another volatile hydrocarbon, or in combination with a volatile silicone. An optional quaternary ammonium compound or water-insoluble conditioning agent is present in an amount of 0% to about 3% by weight individually, and in an amount of 0% to about 5% in total.

The clear conditioning composition also can include coupling agents, such as a nonionic surfactant or a polyhydric compound. An optional coupling agent, or a mixture of coupling agents, is present in an amount of 0% to about 20% by weight of the composition. Exemplary, but nonlimiting nonionic surfactants include N-alkylated-2-pyrrolidones, wherein the alkyl group is a straight chain or branched chain having about 8 to about 16 carbon atoms. Specific N-alkylated-2-pyrrolidones are decyl pyrrolidone (N-decyl-2-pyrrolidone) and lauryl pyrrolidone (N-dodecyl-2-pyrrolidone), available commercially under the tradenames SURFADONE LP-100 and SURFADONE LP-300, respectively, from ISP Corporation, Wayne, N.J. Another exemplary nonionic surfactant is polyoxyethylene (20) oleyl ether, available commercially as BRIJ98 from ICI Americas, Wilmington, Del. The optional polyhydric compound can be a glycol, a triol or a polyol. Specific examples include, but are not limited to ethylene glycol, propylene glycol, butylene glycol, hexylene glycol, diethylene glycol, triethylene glycol, dipropylene glycol, tripropylene glycol, glycerol, or a polyethylene or polypropylene glycol, glycerol, or a polyethylene or polypropylene glycol having an average molecular weight up to approximately 500.

An optional thickener also can be included in the clear conditioning composition to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow)phthalic acid amide, crosslinked maleic anhydride-methyl vinyl ether copolymer, guar gum, xanthan gum and gum arabic.

The carrier of the clear conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Nonaqueous solvents can be present in the clear conditioning composition of the present invention in an amount of about 1% to about 50%, and in particular about 5% to about 25%, by weight of the total weight of the carrier in the composition.

A composition of the present invention is a clear composition that is stable to phase or ingredient separation at a temperature of about 25° C. for an indefinite period of time. For example, a clear conditioning composition of the present invention has demonstrated sufficient stability to phase and ingredient separation at temperatures normally found in commercial product storage and shipping to remain unaffected for periods of one year or more.

A clear, viscous composition has enhanced consumer appeal compared to the present-day, emulsion-type conditioner compositions. The present clear conditioning composition also deposits a sufficient amount of the conditioning compounds on the hair to condition the hair. Previous clear conditioning compositions often did not sufficiently condition the hair because clarity was achieved by using water soluble ingredients, including conditioning compounds, that were easily rinsed from the hair. The present compositions provide both consumer-preferred clarity and good hair conditioning.

To demonstrate the new and unexpected results achieved by the present invention, the following compositions were prepared. The compositions of Examples 1–4 show that at a weight ratio of amidoamine compound to silicone compound of at least 2.8 to 1 a clear conditioning composition is achieved.

| Ingredient | Example 1[1)] | Example 2 | Example 3 | Example 4 |
|---|---|---|---|---|
| Silicone Compound[2)] | .7 | .7 | .7 | .7 |
| Amidoamine[3)] | — | 1.0 | 1.0 | 2.0 |
| Lactic Acid[4)] | .3 | .7 | .7 | .7 |
| Hexylene Glycol | 10.0 | — | 10.0 | — |
| Propylene Glycol | 4.0 | — | 4.0 | — |
| Water | q.s. to 100% | q.s. to 100% | q.s. to 100% | q.s. to 100% |
| pH | 5.2 | 5.5 | 5.4 | 5.5 |
| Appearance | Cloudy | Cloudy | Cloudy | Clear |

[1)]Percentages are active weight percent of each ingredient present in the composition;
[2)]SILQUAT Q-50, available from Siltech, Inc. Norcross, GA, added as a 70% active product in isopropyl alcohol;
[3)]LEXAMINE L-13, lauramidopropyldimethylamine, available from Inolex Corp., Philadelphia, PA. as a 100% active product; and
[4)]Added as an 88% aqueous solution to neutralize the amidoamine and adjust the pH.

The compositions of Examples 1 through 4 show that a clear conditioning composition is achieved when the weight ratio of amidoamine compound to silicone compound is at least 2.8, even in the absence of coupling agent (Example 4). The compositions of Examples 2 and 3 have a weight ratio of amidoamine compound to silicone compound of about 1.4 are cloudy compositions even in the presences of 14% by weight coupling agents (Example 3). Example 1 illustrates that a composition including a silicone compound but absent an amidoamine compound is cloudy at a pH of about 5.2. The amidoamine compound therefore is essential to solubilize the silicone compound and provide a clear conditioning composition.

To further demonstrate a composition the present invention, the composition of Example 5 was prepared. The composition of Example 5 was clear, viscous liquid of good stability and had a pH of about 4.8. The

EXAMPLE 5

| Ingredient | weight percent |
| --- | --- |
| Silicone Compound[2] | 1.00 |
| Amidoamine[3] | 1.00 |
| Lactic Acid[4] | 0.44 |
| Hexylene Glycol | 10.00 |
| Propylene Glycol | 4.00 |
| Cyclomethicone[5] | 1.00 |
| Quaternary Ammonium Compound[6] | 1.50 |
| Protein-based Conditioner[7] | 0.80 |
| Coupling Surfactant[8] | 1.75 |
| Nonionic Surfactant[9] | 0.80 |
| Thickener[10] | 1.15 |
| Fragrance | 0.30 |
| Preservative[11] | 0.25 |
| Dye | q.s. |
| Water | q.s. to 100% |

[5]Silicone SF1173, G.E. Silicones, Waterford, NY, added as a 100% active material;
[6]ADOGEN 432ET, Sherex Chemical Co., Dublin, OH, added as a 75% by weight active material (dicetyldimonium chloride);
[7]MACKPRO WLW, The McIntyre Group, University Park, IL, added as a 40% by weight active material (quaternized wheat protein);
[8]SURFADONE LP300, ISP Chemical Co., Wayne, NJ, added as a 100% active material (N-laurylpyrolidone);
[9]BRIJ 98, ICI Americas, Wilmington, DE, added as a 100% by weight active material (polyoxyethylene (20) oleyl ether);
[10]NATROSOL HHR, Hercules, Inc., Wilmington, DE (hydroxyethylcellulose); and
[11]0.05% KATHON CG Rohm and Haas Co., Philadelphia, PA and 0.20% Glydant, Lonza, Inc., Fairlawn, NJ.

composition of Example 5 compared favorably in appearance and esthetics to the commercial clear conditioning composition sold under the tradename XENON, by Helene Curtis, Inc., Chicago, Ill. Similar conditioning compositions substituting SILQUAT Q-300, ABIL-QUAT 3270 or ABIL-QUAT 3272 for SILQUAT Q-50 also were clear compositions having a consumer-acceptable appearance.

In particular, to demonstrate the improved hair conditioning properties of hair treated with a composition of the present invention, the composition of Example 5 was applied to human hair, and conditioning properties of the hair were compared to the conditioning properties imparted to hair by CLEAN AND CLEAR CONDITIONER, a standard clear conditioner commercially available from Revlon, New York, N.Y. The composition of Example 5 generally performed equal to CLEAN AND CLEAR CONDITIONER, and outperformed CLEAN AND CLEAR conditioner with respect to wet combing and wet feel.

Therefore, the method and composition of the present invention impart hair conditioning properties to treated hair as well as present day clear conditioning compositions and as well as emulsified conditioner compositions. It is both surprising and unexpected for an aqueous composition of the present invention to be a consumer-appealing clear product, to maintain product stability over long storage times, and to impart with such excellent hair conditioning properties to treated hair. The clear compositions of the present invention sufficiently coat the hair with conditioning agents and also are easy to rinse from the hair.

In addition, the method of the present invention provides the further benefits of not leaving the hair tacky or sticky; not forming a crust and therefore providing combability; and providing manageable and styleable hair having body. In addition, after treating the hair with the composition of the present invention, the hair feels natural and thickened, has body, is soft, shiny, manageable and combable. These beneficial effects can be achieved by using an aqueous spray or aqueous solution formulation.

Obviously, many modifications and variations of the invention as hereinbefore set forth can be made without departing from the spirit and scope thereof and therefore only such limitations should be imposed as are indicated by the appended claims.

What is claimed is:

1. A clear hair conditioning composition comprising:
   (a) about 0.4% to about 15% by weight of an amidoamine salt, wherein the amidoamine salt comprises:
   (i) an amidoamine compound having a general structure:

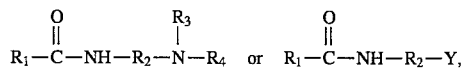

or a mixture thereof, wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety, and
   (ii) a sufficient amount of a suitable acid to neutralize the amidoamine compound and provide a composition pH of about 4 to about 7;
   (b) about 0.1% to about 5% by weight of a silicone compound having at least two quaternary ammonium moieties; and
   (c) an aqueous carrier,
   wherein the amidoamine compound is present in a sufficient amount to provide a clear composition, and
   wherein the amidoamine compound and the silicone compound are present in a weight ratio of amidoamine compound to silicone compound of at least about 2.8 to 1, such that the composition is clear when free of a coupling agent.

2. The composition of claim 1 wherein the amidoamine compound and the silicone compound are present in a weight ratio of amidoamine compound to silicone compound of about 3 to about 4.

3. The composition of claim 1 wherein the amidoamine salt is present in an amount of about 0.7% to about 8% by weight of the composition.

4. The composition of claim 1 wherein the amidoamine salt is present in an amount of about 0.8% to about 5% by weight.

5. The composition of claim 1 wherein the amidoamine compound is selected from the group consisting of lauramidopropyldimethylamine, stearamidopropyldimethylamine, stearamidoethyldiethanolamine, isostearamidopropylmorpholine, stearamidopropylmorpholine, stearamidoethylethanolamine, diethylaminoethylstearamide, isostearamidopropyldimethylamine, cocamidopropyldimethylamine, ricinoleamidopropyldimethylamine, oleamidopropyldimethylamine, behenamidopropyldimethylamine, wheat germamidopropyldimethylamine, palmitamidopropyldimethylamine, stearamidoethyldiethylamine, soyamido-propyldimethylamine, dimethylaminopropyl myristamide, and mixtures thereof.

6. The composition of claim 1 wherein the acid is present in a sufficient amount to neutralize the amidoamine compound and provide a composition pH of about 4.5 to about 6.5.

7. The composition of claim 1 wherein the silicone compound has a general structure:

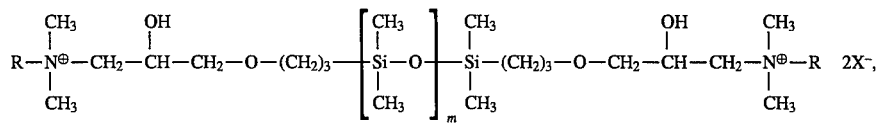

wherein R is an alkyl group having one to about 22 carbon atoms; m is a numeral from about five to about fifty, and X is a water-soluble anion.

8. The composition of claim 7 wherein the silicone compound has the structure:

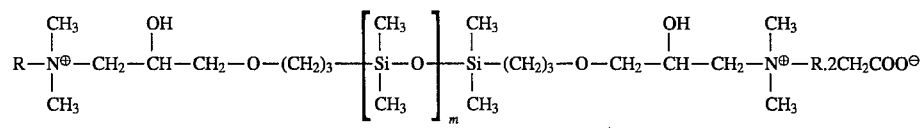

wherein m is a numeral from about 10 to about 30.

9. The composition of claim 1 wherein the silicone compound is Quaternium 80.

10. The composition of claim 1 wherein the silicone compound is present in an amount of about 0.2% to about 4% by weight of the composition.

11. The composition of claim 1 wherein the silicone compound is present in an amount of about 0.2% to about 3% by weight of the composition.

12. The composition of claim 1 wherein the aqueous carrier further comprises about 1% to about 50% by weight relative to the total weight of the carrier of a lower alcohol, a glycol ether, or a combination thereof.

13. The composition of claim 1 wherein the amidoamine compound is lauramidopropyldimethylamine and the silicone compound is Quaternium 80, wherein the amidoamine compound is neutralized with an organic acid.

14. A method of conditioning the hair comprising contacting the hair with a clear conditioning composition for a sufficient time to condition the hair, said composition comprising:

(a) about 0.4% to about 15% by weight of an amidoamine salt, wherein the amidoamine salt comprises:

(i) an amidoamine compound having a general structure:

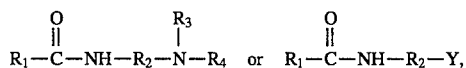

or a mixture thereof, wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety, and (ii) a sufficient amount of a suitable acid to neutralize the amidoamine compound and provide a composition pH of about 4 to about 7;

(b) about 0.1% to about 5% by weight of a silicone compound having at least two quaternary ammonium moieties; and (c) an aqueous carrier, wherein the amidoamine compound is present in a sufficient amount to provide a clear composition, and wherein the amidoamine compound and the silicone compound are present in a weight ratio of amidoamine compound to silicone compound of at least about 2.8 to 1, such that the composition is clear when free of a coupling agent.

15. The method of claim 14 further comprising rinsing the hair with water after contacting the hair with the clear conditioning composition.

16. The method of claim 14 wherein the silicone compound has a general structure:

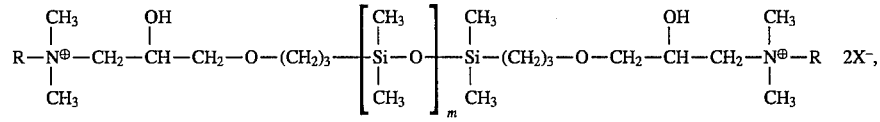

wherein R is an alkyl group having one to about 22 carbon atoms; m is a numeral from about five to about fifty; and X is a water-soluble anion.

17. The method of claim 16 wherein the silicone compound has the structure:

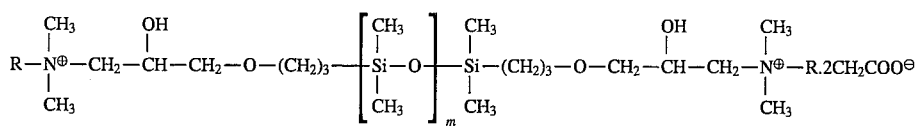
wherein m is a numeral from about 10 to about 30.
18. The method of claim 14 wherein the silicone compound is Quaternium 80.
19. The method of claim 14 wherein the amidoamine compound is lauramidopropyldimethylamine and the silicone compound is Quaternium 80, wherein the amidoamine compound is neutralized with an organic acid.
* * * * *

UNITED STATES PATENT AND TRADEMARK OFFICE
CERTIFICATE OF CORRECTION

PATENT NO. : 5,556,615

DATED : September 17, 1996

INVENTOR(S) : Ben Janchitraponvej, William J. Brown and Patricia Lee

It is certified that error appears in the above-identified patent and that said Letters Patent is hereby corrected as shown below:

Column 9, last structure on page, at end of Structure (VI), "R.2CH$_2$COO$^-$" should be --R·2CH$_2$COO$^-$ --.

Column 10, line 6, line starting with "In particular," should be indented as a new paragraph.

Column 15, line 2, "have" should be --having--.

Column 15, line 10, insert "of" between "composition" and "the".

Columns 17, 18, the structure in claim 8, "R.2CH$_2$COO$^-$" should be --R·2CH$_2$COO$^-$ --.

Columns 19, 20, the structure in claim 17, "R.2CH$_2$COO$^-$" should be --R·2CH$_2$COO$^-$ --.

Signed and Sealed this

Eighteenth Day of March, 1997

*Attest:*

BRUCE LEHMAN

*Attesting Officer*   *Commissioner of Patents and Trademarks*